United States Patent
Zhao et al.

(10) Patent No.: US 8,569,508 B2
(45) Date of Patent: Oct. 29, 2013

(54) SYNTHETIC METHOD FOR MONTELUKAST SODIUM INTERMEDIATE

(75) Inventors: Zhiquan Zhao, Linyi (CN); Haixin Wang, Linyi (CN); Zengxue Wang, Linyi (CN)

(73) Assignee: Shandong New Time Pharmaceutical Co., Ltd., Shandong (CN)

( * ) Notice: Subject to any disclaimer, the term of this patent is extended or adjusted under 35 U.S.C. 154(b) by 68 days.

(21) Appl. No.: 13/393,488

(22) PCT Filed: Aug. 24, 2010

(86) PCT No.: PCT/CN2010/076281
§ 371 (c)(1),
(2), (4) Date: Mar. 16, 2012

(87) PCT Pub. No.: WO2011/026398
PCT Pub. Date: Mar. 10, 2011

(65) Prior Publication Data
US 2012/0165535 A1  Jun. 28, 2012

(30) Foreign Application Priority Data

Sep. 2, 2009  (CN) .......................... 2009 1 0168970

(51) Int. Cl.
*C07D 215/38* (2006.01)
(52) U.S. Cl.
USPC ............................ 546/174; 546/176; 546/180

(58) Field of Classification Search
USPC .......................................... 546/174, 176, 180
See application file for complete search history.

(56) References Cited

U.S. PATENT DOCUMENTS 5,869,673 A * 2/1999 Tung et al. .................... 546/172

FOREIGN PATENT DOCUMENTS

| CN | 101638381 | 2/2010 |
| WO | 2006/021974 | 3/2006 |

OTHER PUBLICATIONS

International Search Report, mailed Dec. 2, 2010, for application No. PCT/CN2010/076281.

* cited by examiner

*Primary Examiner* — D M Seaman
(74) *Attorney, Agent, or Firm* — Workman Nydegger

(57) ABSTRACT

A synthesis method for preparing Montelukast sodium intermediate 2-(2-(3-(2-(7-chloro-2-quinolyl)vinyl)phenyl-3-oxopropyl)phenyl) propanol is provided. In this method, the target compound is prepared by condensing the starting materials 7-chloroquinaldine and 3-cyanobenzaldehyde, and then reacting the resultant product with 2-(2-ortho-(2-haloethyl)-phenylpropyl)tetrahydropyrane ether. The present invention can easily obtain start materials and is applicable for mass production.

20 Claims, No Drawings

SYNTHETIC METHOD FOR MONTELUKAST SODIUM INTERMEDIATE

CROSS REFERENCE TO RELATED APPLICATIONS

The present application is a U.S. National Stage of International Application No. PCT/CN2010/076281, filed Aug. 24, 2010, designating the United States, and claiming priority to Chinese Patent Application No. 200910168970.1, filed Sep. 2, 2009. Both of the aforementioned applications are incorporated herein in their entirety.

TECHNICAL FIELD

This invention belongs to the field of chemical synthesis of pharmaceuticals. The present invention relates to a method for synthesizing a compound, especially a synthesis method for preparing Montelukast sodium intermediate.

BACKGROUND ART

Montelukast sodium has a chemical name of sodium 1-(((1-(R)-(3-(2-(7-chloro-2-quinolyl)-vinyl)phenyl)-3-(2-(1-hydroxy-1-methylethyl)phenyl)propyl)thio))methyl)cyclopropyl-acetate, and its structure formula as follows:

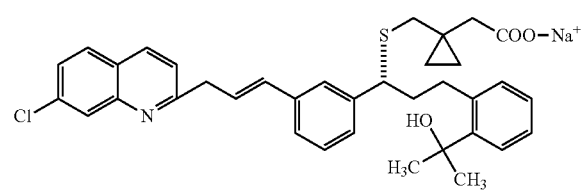

Montelukast sodium can be useful in treating asthma, and also can be useful as an anti-allergic drug, etc. This compound was first synthesized by Merck Frosst Canada Ltd. located at Quebec, Canada. In the Chinese Patent Application CN1061407A, Merck Frosst Canada Ltd. disclosed the structure and the synthesis method of the compound by reacting 2-(2-3(R)-(3-2-(7-chloro-2-quinolyl)-vinyl)phenyl)-3-(hydroxy)propyl)phenyl) propanol with 1-(mercaptomethyl)-cyclopropylethyl acetate.

CN1420113A disclosed another synthesis method by reacting 2-(2-3(S)-(3-2-(7-chloro-2-quinolyl)-vinyl)phenyl)-3-(sulfydryl)propyl)phenyl)propanol with 2-(1-bromomethyl)-cyclopropylethyl acetate.

CN101081834A disclosed that said compound was prepared by reacting 2-(2-3(R)-(3-2-(7-chloro-2-quinolyl)-vinyl)phenyl)-3-(hydroxy)propyl)phenyl)propanol having a leaving group with lithium salt of 1-(mercaptomethyl)cyclopropylacetate.

Among the synthesis methods for Montelukast sodium disclosed by the prior arts, most of the methods use a basic compound, methyl 2-(2-3(R or S)-(3-2-(7-chloro-2-quinolyl)-vinyl)phenyl)-3-(hydroxy)propyl)phenyl) propanol, as the staring material, which was synthesized from the intermediate compounds, methyl 2-(2-(3-(2-(7-chloro-2-quinolyl)vinyl) phenyl)-3-oxopropyl)benzoate, or methyl 2-(2-(3-(2-(7-chloro-2-quinolyl)vinyl)phenyl)-3-hydroxypropyl)benzoate. In the prior arts, the kind of intermediate compounds was synthesized by the following several approaches:

For example, J. Org. Chem. Vol. 61, No. 10, 1996, 3398-3405 disclosed that 7-chloro-2-vinyl quinoline and methyl 2-(3-(3-bromomethylphenyl)-3-oxopropyl)) benzoate as the staring materials were reacted by a palladium-catalyzed coupling reaction to obtain methyl 2-(2-(3-(2-(7-chloro-2-quinolyl)vinyl)phenyl)-3-oxopropyl)benzoate.

In the method F provided by EP480717, ethyl 3-(3-(2-(7-chloro-2-quinolyl)vinyl)phenyl)-3-oxopropionate reacted with methyl iodomethylbenzoate, and then decarboxylated, to generate methyl 2-(2-(3-(2-(7-chloro-2-quinolyl)vinyl)phenyl)-3-oxo propyl)benzoate.

In another method K provided by EP480717, 7-chloroquinaldine as the staring material reacted with isophthalaldehyde to generate 3-(2(E)-2-(7-chloroquinazolinyl)vinyl)benzaldehyde, then reacted with vinylmagnesium bromide to perform a Grignard Reaction, and then reacted with ethyl 2-bromobenzoate, to generate methyl 2-(2-(3-(2-(7-chloro-2-quinolyl)vinyl)phenyl)-3-oxopropyl)benzoate.

Among the above stated synthesis methods for preparing the intermediate compounds, expensive metal palladium was often used, thus making the production cost increase; or the Grignard reactions were performed many times, which require strict and complicate reaction conditions and thus need to be strictly controlled, as well as also generated more byproducts undesired; meanwhile, there was a problem that the obtained products cannot be stored for a long time; therefore, the prior synthesis methods were not applicable for mass production.

In addition, although there are many synthesis methods for preparing the above-mentioned Montelukast sodium intermediate in the prior arts, the synthesis methods for another important Montelukast sodium intermediate shown as formula, 1,2-(2-(3-(2-(7-chloro-2-quinolyl)vinyl)phenyl)-3-oxopropyl)phenyl)propanol, were seldom recorded. Under the existence of a chiral reductant, the latter intermediate compound can be selectively converted into a desired chiral mother nucleus, and thus has an extensive prospect of application.

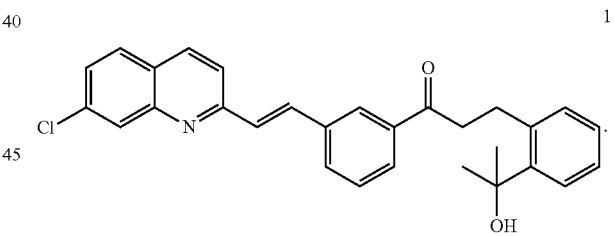

Therefore, there is a need to research and develop a new synthesis method for preparing the Montelukast sodium intermediate shown as formula 1,2-(2-(3-(2-(7-chloro-2-quinolyl)vinyl)phenyl)-3-oxopropyl)phenyl)propanol, which is applicable for mass production.

SUMMARY OF THE INVENTION

Synthesis methods provided in the prior art are not applicable to mass production of the Montelukast sodium intermediate of formula 1,2-(2-(3-(2-(7-chloro-2-quinolyl)vinyl) phenyl)-3-oxopropyl)phenyl)propanol.

In order to overcome the problems existing in the prior art, one object of the present invention is to provide a synthesis method for preparing Montelukast sodium intermediate, which is applicable for mass production of the Montelukast sodium intermediate of formula 1, 2-(2-(3-(2-(7-chloro-2-quinolypvinyl)phenyl)-3-oxopropyl)phenyl)propanol.

The present invention can be realized through the following technical solutions:

A synthesis method for preparing the Montelukast sodium intermediate of formula 1,2-(2-(3-(2-(7-chloro-2-quinolyl)vinyl)phenyl)-3-oxopropyl)phenyl)propanol, comprising the steps of:

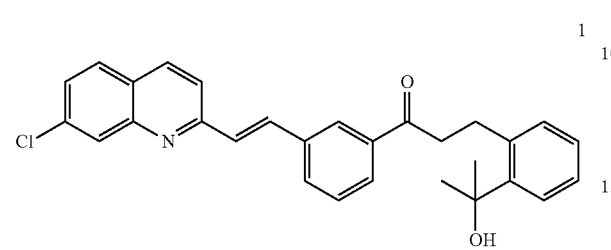

f. Reacting the compound of formula 9 with the compound of formula 4, under the existence of metal magnesium and an inert solvent, to generate the target product, 2-(2-(3-(2-(7-chloro-2-quinolyl)vinyl)phenyl)-3-oxopropyl)phenyl)propanol, through the following reaction:

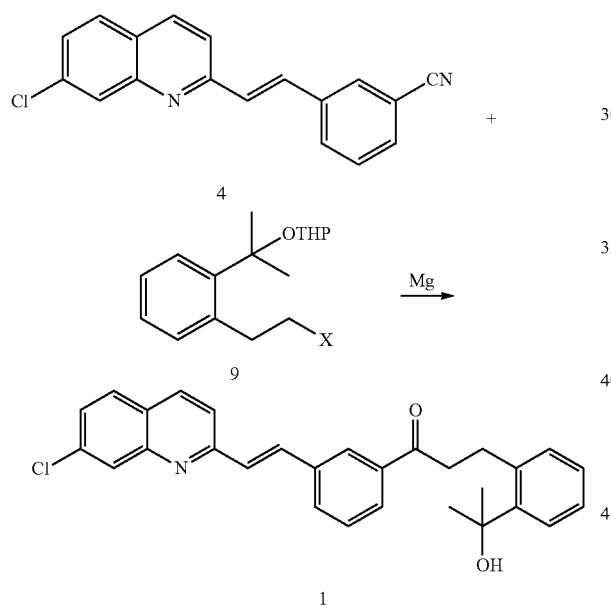

In the above method, the compound of formula 4 as one of the starting materials is stable in air and can be stored for a long time without any chemical changes, and thus is easy for storage and transport. The compound of formula 9, as another of the starting materials, also has a stable structure. Furthermore, no expensive metal palladium is needed in this method. Therefore, this method can adapt the need of mass production.

In the above method, the starting materials including the compound of formula 4 and the compound of formula 9 can be prepared in accordance with the synthesis methods provided in the prior art. For example, J. Scott Sawyer et al. (Optimization of the Quinoline and Substituted benzyl Moieties of a Series of Phenyltetrazole Leukotriene D4 Receptor Antagonists, J. Med. Chem. 1992, 35, 1200-1209) disclosed a synthesis route for preparing the compound of formula 4. In addition, the compound of formula 4 and the compound of formula 9 can be prepared in accordance with the method revealed in the present invention, which further proves the industrial value of the present invention. Therefore, in the preferred embodiments of the present invention, the method in accordance with the invention can adopt the following reaction routes:

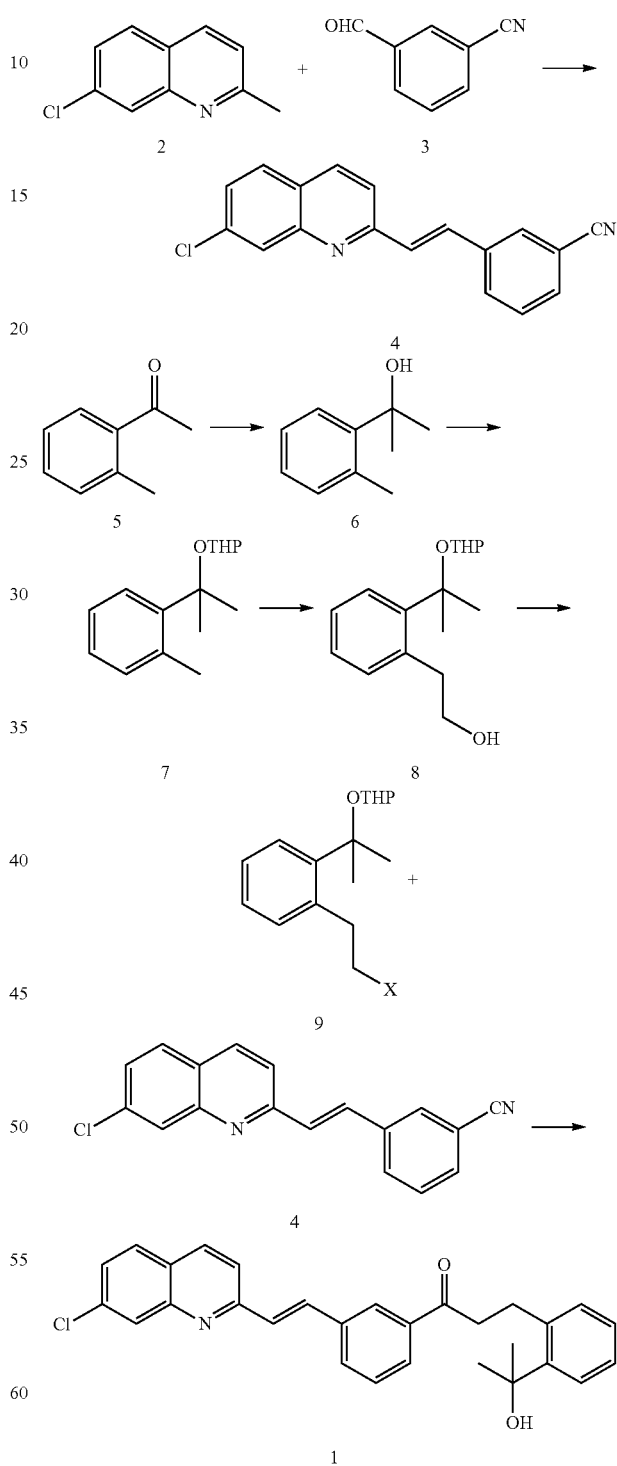

Correspondingly, in the preferred embodiments of the present invention, the method of the invention can comprise the following steps:

a. Condensing 7-chloroquinaldine (the compound of formula 2) and 3-cyanobenzaldehyde (the compound of formula 3) under the existence of acetic anhydride and sodium acetate to generate 3-(2-(7-chloro-2-quinolyl)vinyl)benzonitrile (the compound of formula 4), through the following reaction:

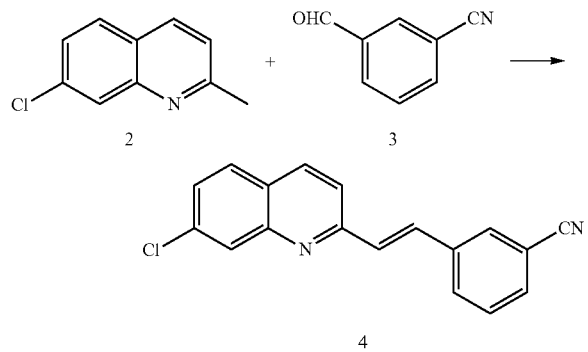

In this step, the solvent used in the reaction is preferably one or more selected from the group consisting of dimethyl sulfoxide (DMSO), dimethyl fomamide (DMF), dimethyl acetylamide (DMA) and hexamethyl phosphoramide, and more preferably DMF. The reaction temperature varies with the variation of the reactants and the solvent. Usually the reaction temperature is 80° C.-200° C., preferably 120° C.-140° C.

Reacting ortho-methylphenylethanone (the compound of formula 5) in an inert solvent under the existence of methylmagnesium halide to generate 2-orthomethylphenyl-2-propanol (the compound of formula 6), through the following reaction:

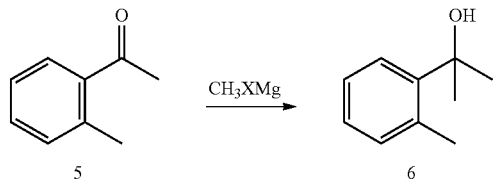

In this step, the solvent used in the reaction is one or more selected from the group consisting of benzene and its homologue, tetrahydrofuran, 2-methyl tetrahydrofuran, diethyl ether, isopropyl ether and glycol dimethyl ether. Methylmagnesium halide can be methylmagnesium chloride or methylmagnesium bromide. TLC is used to monitor the end of the reaction, with the developer as n-hexane:ethyl acetate=4:1 (volume ratio). Considering that methylmagnesium bromide is more expensive than ortho-methylphenylethanone, excess phenylethanone is used; the molar ratio of methylmagnesium halide:ortho-methylphenylethanone (the compound of formula 5) equals to 1 mol:(1.0-1.5 mol), while the reaction temperature is 20° C.-30° C. The temperature in the reaction bottle remains below 0° C. when the solution of methylmagnesium bromide is added dropwise into the reaction bottle.

c. Reacting the compound of formula 6 under the existence of a catalyst with dihydropyran to generate hydroxyl-protected 2-(2-orthomethylphenylpropyl)tetrahydropyran ether (the compound of formula 7), through the following reaction:

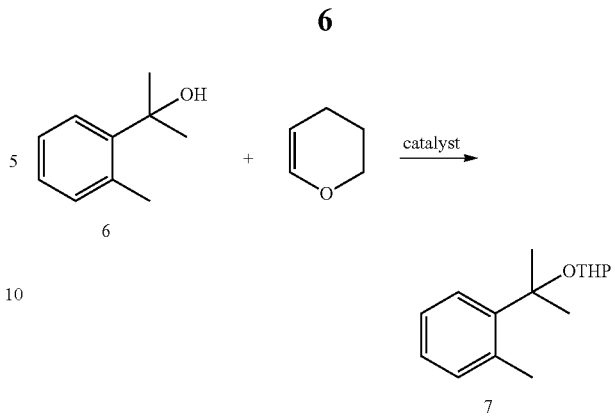

In this step, the catalyst used in the reaction can be one or more selected from the group consisting of triphenylphosphine hydrobromide, tri(t-butyl)phosphine hydrobromide, hydrochloric acid (including hydrogen chloride gas), hydrobromic acid (including hydrogen bromide gas), phosphorus oxychloride, p-toluenesulfonic acid and pyridinium thereof, and boron trifluoride-diethyl ether, preferably triphenylphosphine hydrobromide. The molar ratio of the reactants is 2-orthomethylphenyl-2-propanol (the compound of formula 6):dihydropyran:catalyst=1 mol:2-6 mol:0.1-1 mol. During adding the reactants, the half of the desired amounts of dihydropyran and triphenylphosphine hydrobromide are first added, and after refluxing and stirring the reactants for 24 hours, the remaining half of the desired amounts of dihydropyran and triphenylphosphine hydrobromide are then added in and the reactants are stirred and heated to reflux until the reaction is complete.

d. Reacting the compound of formula 7 with formaldehyde or paraformaldehyde under the existence of a catalyst, to generate 2-(2-ortho(2-hydroxyethyl)phenylpropyl)) tetrahydropyran ether (the compound of formula 8), through the following reaction:

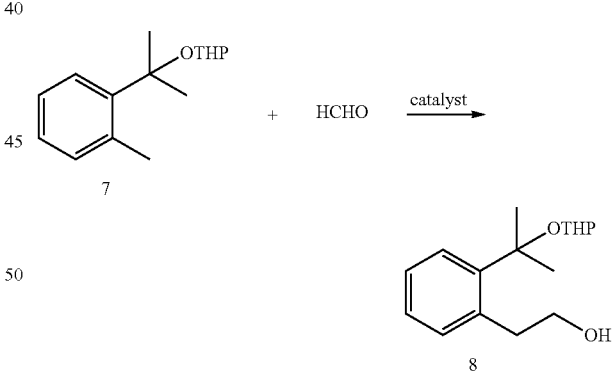

In this step, the catalyst used in the reaction is one selected from the group consisting of alkali metal hydroxide such as sodium hydroxide, alkali metal carbonate, and organic quaternary ammonium hydroxide, preferably organic quaternary ammonium hydroxide. The solvent used in the reaction is polar solvent, e.g., one or more selected from the group consisting of dimethyl sulfoxide (DMSO), dimethyl fomamide (DMF), dimethyl acetylamide (DMA), and water, preferably DMSO. The molar ratio of the reactants is: 2-(2-orthomethylphenylpropyl)tetrahydropyrane ether (the compound of formula 7):catalyst:formaldehyde=1 mol:(0.001-0.1 mol): (1-4 mol). The reaction temperature is 20° C.-100° C., preferably 55° C.-65° C., while the reaction time is 1.5-24 hours. During adding the reactants, a portion of the catalyst and formaldehyde are first added, and after each 0.5-2 hours for reaction, the remaining catalyst and formaldehyde are evenly batch-added.

The reaction temperature varies with the variation of the reactants and the solvent. When the reaction temperature is relative high, diol compounds will be generated, and when the reaction time is relative long, corresponding dihydroxymethylated products will increase. The invention can decrease the generation of dihydroxy compounds by batch-adding the catalyst and formaldehyde, and thus achieves a good effect.

e. Adding dropwise a halogenating reagent into the solution containing the compound of formula 8, to generate 2-(2-ortho(2-ethyl)phenylpropyl)tetrahydropyran ether (the halogenated compound of formula 9), through the following reaction:

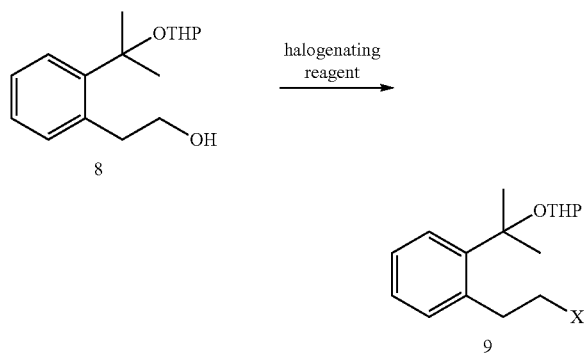

In this step, the reaction temperature is −5° C.-10° C.; the solvent used in the reaction is one or more selected from the group consisting of benzene, diethyl ether, dichloromethane, chloroform, carbon tetrachloride, dioxane, and hexamethyl phosphoramide, preferably dichloromethane; and the halogenating reagent used in the reaction is one or more selected from the group consisting of thionyl chloride, hydrochloric acid-zinc chloride, phosphorus pentachloride, phosphorus oxychloride, hydrogen bromide and phosphorus tribromide, preferably phosphorus tribromide.

f. Reacting the halogenated compound of formula 9 with the compound of formula 4 under the existence of metal magnesium and an inert solvent, to generate the target compound of formula 1, 2-(2-(3-(2-(7-chloro-2-quinolyl)vinyl)phenyl)-3-oxopropyl)phenyl) propanol, through the following reaction:

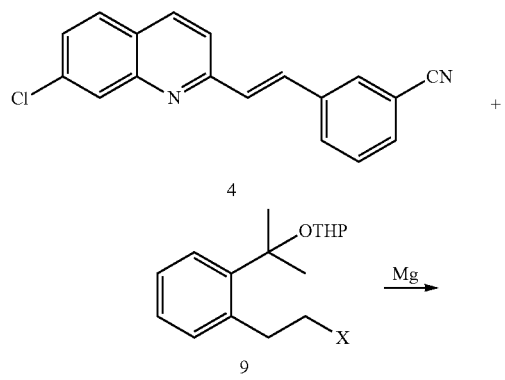

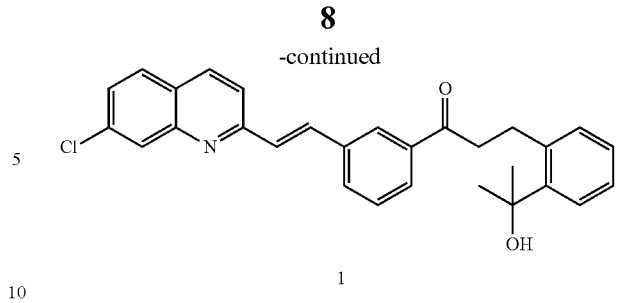

In this step, under the protection of nitrogen, some newly-polished magnesium strips are added into the solution containing 2-(2-ortho(2-bromoethyl)phenylpropyl)tetrahydropyran ether (the compound of formula 9). When the reaction is complete, the excess magnesium strips are filtered out for use in the next step. 3-(2-(7-chloro-2-quinolyl)vinyl)benzonitrile (the compound of formula 4) is dissolved in anhydrous tetrahydrofuran and then the solution is cooled down to below 0° C. The forementioned prepared Grignard reagent dissolved in the tetrahydrofuran is added dropwise slowly. During the adding dropwise, the temperature of the reactant solution is controlled with the range of 0° C.-5° C. And after the addition, the reactant solution is raised slowly to reflux. When the reaction is complete, hydrochloric acid (6 mol/L) is added dropwise into the reactant solution, with a slow heating to reflux and stir until the addition is finished. The molar ratio of the reactants is: 2-(2-ortho(2-bromoethyl)phenylpropyl) tetrahydropyrane ether (the compound of formula 9):metal magnesium:3-(2-(7-chloro-2-quinolyl)vinyl)benzonitrile (the compound of formula 4)=1 mol:(1.2-2.5 mol): (0.8-1 mol).

The present invention provides a method, comprising: meta-cyanobenzaldehyde (the compound of formula 3) is used as the starting material to condense with 7-chloroquinaldine (the compound of formula 2) to generate the intermediate 3-(2-(7-chloro-2-quinolyl)vinyl)benzonitrile (the compound of formula 4), which is stable in air and can be stored for a long time without any chemical changes and thus is easy for storage and transportation; Then ortho-methylphenylethanone (the compound of formula 5) for industry use is used as the starting material to react with Grignard reagent to generate 2-ortho-methylphenyl-2-propanol, which is then protected by hydroxyl using dihydropyran; The protected compound is hydroxymethylated under alkali condition and then is halogenated to generate a halide (the compound of formula 9); The compound of formula 9 condenses with the intermediate compound of formula 4 in an inert solvent and then is hydrolyzed to generate the target compound. The whole process is simple for operation and easy for control. Moreover, the reaction condition is not rigorous, the start materials are cheap and thus the method of this invention is applicable for mass production.

The present invention has the following advantageous technical effects:

1. The main start materials such as meta-cyanobenzaldehyde and ortho-methylphenylethanone can be easily obtained with a cheap price;

2. Although the present invention goes through 6 steps of reactions, the target intermediate compound (the compound of formula 1) can be generated with a yield of 40% or higher as well as a high purity;

3. No expensive metal palladium is needed, and thus the product cost is reduced;

4. The process of the invention is stable and controllable, easy for operation and applicable for mass production of Montelukast sodium intermediate.

PREFERABLE EMBODIMENTS

Now the advantageous effects of the present invention are described by reference to the following embodiments, which should be understood as examples for illustration purpose, rather than limiting the scope of the present invention. Meanwhile, apparent changes and modifications made by one skilled in this art shall fall into the scope of the invention.

EXAMPLE 1

Preparation of 3-(2-(7-chloro-2-quinolyl)vinyl)benzonitrile (the Compound of Formula 4)

Under the protection by nitrogen, meta-cyanobenzaldehyde (137.6 g, 1.05 mol), 7-chloroquinaldine (177 g, 1.0 mol) and sodium acetate (82 g) are added into 1000 ml of acetic anhydride, and the resulted mixture solution is stirred and heated to 125-135° C. for 24 hours. After distilling out the most of acetic anhydride, 300 ml of water is added into the residue, and then extracted by ethyl acetate (500 ml×3), washed with saturated saline water, dried with anhydrous sodium sulfate and condensed in the vacuum. The resulted residue is then purified through Flash Column Chromatography to obtain 266.8 g of the title compound, with a yield of 92%.

$^1$H NMR (DMSO$^d$) 8.38 (d, J=9 Hz, 1 H), 8.10 (d, J=9 Hz, 1 H), 7.50-8.08 (m, 9 H);

IR (KBr, cm$^1$), 2230, 1597, 1504, 976, 824;

HRMS calculated for (M+) $C_{18}H_{11}ClN_2$ 290.0611. found 290.0617.

EXAMPLE 2

Preparation of 3-(2-(7-chloro-2-quinolyl)vinyl)benzonitrile (the Compound of Formula 4)

Under the protection by nitrogen, meta-cyanobenzaldehyde (137.6 g, 1.05 mol), 7-chloroquinaldine (177 g, 1.0 mol) and sodium acetate (82 g) are added into 200 ml of acetic anhydride and 800 ml of dimethyl fomamide (DMF), and the resulted mixture solution is stirred and heated to reflux for 24 hours. After distilling the most solvent, 300 ml of water is added into the residue, and then extracted by ethyl acetate (500 ml×3), washed with saturated saline water, dried with anhydrous sodium sulfate and condensed in the vacuum. The resulted residue is then purified through Flash Column Chromatography to obtain 241 g of the title compound, with a yield of 83%.

Example 3

Preparation 2-ortho-methylphenyl-2-propanol (the Compound of Formula 6)

Under the protection by nitrogen, ortho-methylphenylethanone (134 g, 1.0 mol) is dissolved in 1000 ml of tetrahydrofuran and then cooled to −5° C., into which 2 M methylmagnesium bromide in tetrahydrofuran (550 ml) is slowly added dropwise at below 0° C. After the addition, the reactant solution is stirred at room temperature for 3 hours under the detection of TLC. When the reaction is complete, 200 ml of saturated NH$_4$Cl solution is slowly added dropwise into the reactant solution and stirred until no bubbling from the solution. The resulted solution is then extracted by dichloromethane (500 ml×3), the extracts are combined, dried by anhydrous sodium sulfate, absorbed by activated carbon, filtered, and then the solvent is distilled out using rotary evaporator to obtain 132 g of 2-ortho-methylphenyl-2-propanol as a light yellow sticky liquid, with a yield of 88%.

$^1$H NMR (CDCl3) 7.18-7.42 (4H, m), 4.38 (1H'brs), 2.36 (3H, s), 1.33 (6H, s)

EXAMPLE 4

Preparation of 2-ortho-methylphenyl-2-propanol (the Compound of Formula 6)

Under the protection by nitrogen, ortho-methylphenylethanone (134 g, 1.0 mol) is dissolved in 1000 ml of tetrahydrofuran and then cooled to −5° C., into which 2M methylmagnesium chloride in tetrahydrofuran (550 ml) is slowly added dropwise at below 0° C. After the addition, the reactant solution is stirred at room temperature for 4 hours under the detection by TLC. When the reaction is complete, 200 ml of saturated NH$_4$Cl solution is slowly added dropwise into the reactant solution and stirred until no bubbling from the solution. The reactant solution is then extracted by dichloromethane (500 ml×3), the extracts are combined, dried by anhydrous sodium sulfate, absorbed by activated carbon, filtered and then the solvent is distilled using rotary evaporator to obtain 124 g of 2-ortho-methylphenyl-2-propanol as a light yellow sticky liquid, with a yield of 82.6%.

EXAMPLE 5

Preparation of 2-(2-orthomethylphenylpropyl)tetrahydropyran ether (the Compound of Formula 7)

The compound of formula 6 (75 g, 0.5 mol) is added into 500 ml of dry dichloromethane, and then dihydropyran (84.0 g, 1.0 mol) and triphenylphosphine hydrobromide (3.43 g, 0.01 mol) are added therein with stir. After the reactant solution is stirred and refluxed for 24 hours, another portion of dihydropyran (84.0 g, 1.0 mol) and triphenylphosphine hydrobromide (3.43 g, 0.01 mol) is added in. The reaction solution is stirred and refluxed for 24 hours. When the reaction is complete, the reactant solution is condensed. The resulted residue is purified through silica column chromatography using methylbenzene as eluent, and collected the product phase and obtained 108 g of the title compound as oil, with a yield of 92%.

EXAMPLE 6

Preparation 2-(2-ortho-(2-hydroxyethyl)phenylpropyl)tetrahydropyrane ether (the Compound of Formula 8)

The compound of formula 7 (58.5 g, 0.25 mol) and paraformaldehyde (3 g, 0.1 mol) are added into 50 ml of DMSO, and then 1 ml of trimethyl-benzyl ammonium hydroxide (30%, in methanol) is added dropwise into the reactant solution, the reactant solution becomes deep brown. Maintaining at 60-65° C., paraformaldehyde (3 g, 0.1 mol) and 0.5 ml of trimethylbenzyl ammonium hydroxide (30%, in methanol) are added into the reactant solution every one hour till the amount of paraformaldehyde added in reaches 12 g. When the reaction is complete, the PH of the solution is adjusted to 6-8. The most of DMSO is distilled, and 100 ml of saturated sodium chloride aqueous solution is added into the residue, which is then extracted by ethyl acetate, and separated and purified through column chromatography to obtain 51.5 g of the title compound as a light yellow dope, with a yield of 78%.

EXAMPLE 7

Preparation of 2-(2-ortho-(2-hydroxyethyl)phenyl-propyl)tetrahydropyrane ether (the Compound of Formula 8)

The compound of formula 7 (58.5 g, 0.25 mol) and paraformaldehyde (3 g, 0.1 mol) are added into 50 ml of DMSO, and then 1 ml of tetramethyl ammonium hydroxide (40%, aqueous solution) is added dropwise into the reactant solution, the reactant solution becomes deep brown. Maintaining at 60-65° C., paraformaldehyde (3 g, 0.1 mol) and 0.5 ml of tetramethyl ammonium hydroxide (40%, aqueous solution) are added into the reactant solution every one hour till the amount of paraformaldehyde added in reaches 12 g. When the reaction is complete, the PH of the solution is adjusted to 6-8. The most of DMSO is distilled, and 100 ml of saturated sodium chloride aqueous solution is added into the residue, which is then extracted by ethyl acetate, and separated and purified through column chromatography to obtain 47.7 g of the title compound as a light yellow dope, with a yield of 72.3%.

EXAMPLE 8

Preparation of 2-(2-ortho-(2-hydroxyethyl)phenyl-propyl)tetrahydropyrane ether (the Compound of Formula 8)

The compound of formula 7 (58.5 g, 0.25 mol), paraformaldehyde (3 g, 0.1 mol) and sodium phenolate (0.70 g, 0.006 mol) are added into 50 ml of DMSO. The reactant solution becomes deep brown. Maitaining at 60-65° C., paraformaldehyde (3 g, 0.1 mol) is added into the reactant solution every two hours till the amount of paraformaldehyde added in reaches 12 g. When the reaction is complete, the PH of the solution is adjusted to 6-8. The most of DMSO is distilled, and 100 ml of saturated sodium chloride aqueous solution is added into the residue, which is then extracted by ethyl acetate, and separated and purified through column chromatography to obtain 41.6 g of the title compound as a light yellow dope, with a yield of 63%.

EXAMPLE 9

Preparation of 2-(2-ortho-(2-bromoethyl)phenylpro-pyl)tetrahydropyrane ether (the Compound of Formula 9)

The compound of formula 8 (26.4 g, 0.1 mol) is dissolved in 300 ml of diethyl ether and then cooled to 0° C. Then phosphorus tribromide (3.8 ml, 0.04 mol) is slowly added dropwise into the reactant solution at below 5° C. After the addition, the solution is stirred at room temperature for 5 hours. When the reaction is complete, saturated NaHCO$_3$ aqueous solution is added dropwise into the solution to adjust the PH to neutral, which is then extracted by diethyl ether (300 ml×3). The extracts are combined, dried by anhydrous magnesium sulfate, condensed under reduced pressure to obtain 32 g of the title compound (HPLC 99.2%), with a yield of 98%.

EXAMPLE 10

Preparation of 2-(2-ortho-(2-bromoethyl)phenylpro-pyl)tetrahydropyrane ether (the Compound of Formula 9)

The compound of formula 8 (26.4 g, 0.1 mol) is dissolved into 300 ml of toluene and then cooled to 0° C. Then hydrobromic acid solution (16 g, 48%) is added dropwise slowly into the reactant solution at below 5° C. After the addition, the solution is stirred over night. When the reaction is complete, saturated NaHCO$_3$ aqueous solution is added dropwise into the reactant solution to adjust the PH to neutral, which is then extracted by diethyl ether (300 ml×3). The extracts are combined, dried by anhydrous magnesium sulfate, condensed under reduced pressure to obtain 30.9 g of the title compound, with a yield of 95%.

EXAMPLE 11

Preparation of 2-(2-ortho-(2-chloroethyl)phenylpro-pyl)tetrahydropyrane ether (the Compound of Formula 9)

The compound of formula 8 (26.4 g, 0.1 mol) is dissolved into 300 ml of dichloromethane and cooled to 0° C. Then 8 ml of thionyl chloride is slowly added dropwise into the reactant solution at below 5° C. After the addition, the solution is stirred at room temperature for 5 hours. When the reaction is complete, saturated NaHCO$_3$ aqueous solution is added dropwise into the reactant solution to adjust the PH to neutral, which is then extracted by dichloromethane (300 ml×3). The extracts are combined, dried by anhydrous magnesium sulfate, condensed under reduced pressure to obtain 27 g of the title compound, with a yield of 95%.

EXAMPLE 12

Preparation of 2-(2-ortho-(2-chloroethyl)phenylpro-pyl)tetrahydropyrane ether (the Compound of Formula 9)

The compound of formula 8 (26.4 g, 0.1 mol) is dissolved into 300 ml of dichloromethane and cooled to 0° C. Then phosphorus tribromide (9 g) is slowly added dropwise into the reactant solution at below 5° C. After the addition, the solution is stirred at room temperature for 5 hours. When the reaction is complete, saturated NaHCO$_3$ aqueous solution is added dropwise into the reactant solution to adjust the PH to neutral, which is then extracted by dichloromethane (300 ml×3). The extracts are combined, dried by anhydrous magnesium sulfate, condensed under reduced pressure to obtain 32 g of the title compound, with a yield of 99%.

EXAMPLE 13

Preparation of 2-(3-(3-(2-(7-chloro-2-quinolyl)vinyl)phenyl)-3-oxopropyl)phenyl)-2-propoxy)tetrahydro-pyrane (the Compound of Formula 1)

Under the protection by nitrogen, newly-polished magnesium strips (2.16 g, 0.09 mol) are added into 60 ml of tetrahydrofuran containing 2-(2-ortho(2-bromoethyl)phenylpropyl)

tetrahydropyran ether (16.3 g, 0.06 mol). When the reaction is complete, excess magnesium strips are filtered for use in the next step. The compound 3-(2-(7-chloro-2-quinolyl)vinyl) benzonitrile (14.5 g, 0.05 mol) is dissolved into 100 ml of tetrahydrofuran and cooled to 0° C. Then the Grignard reagent dissolved in tetrahydrofuran prepared above is added dropwise slowly into the cooled solution at below 5° C. After the addition, the resultant solution is stirred and heated to reflux for 3 hours. When the reaction is complete, 30 ml of hydrochloric acid solution (6 mol/L) is added dropwise into the reactant solution, the mixture solution is stirred and heated to reflux for 6 hours. Then saturated $Na_2CO_3$ aqueous solution is added dropwise into the solution to adjust the PH to neutral, which is then extracted by ethyl acetate (100 ml×3). The extracts are combined, dried by anhydrous magnesium sulfate, condensed under reduced pressure to obtain 18.9 g of the title compound, with a yield of 70%.

HRMS calculated for (M+) C29H26ClNO2 455. 1652. found 455.1639

The invention claimed is:

1. A synthesis method for preparing Montelukast sodium intermediate, 2-(2-(3-(2-(7-chloro-2-quinolyl)vinyl)phenyl-3-oxopropyl)phenyl) propanol, as shown in the following formula 1, said method comprising the following steps of:

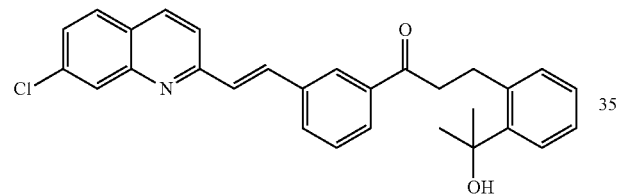

(f) Reacting the compound of formula 9 with the compound of formula 4 under the existence of metal magnesium and an inert solvent, to generate the target product of formula 1, 2-(2-(3-(2-(7-chloro-2-quinolyl)vinyl) phenyl-3-oxopropyl)phenyl) propanol, through the following reaction:

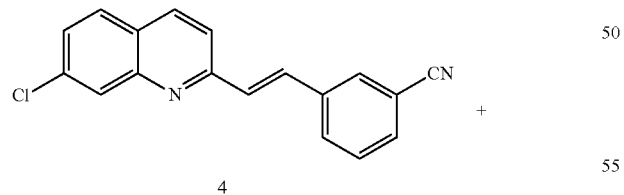

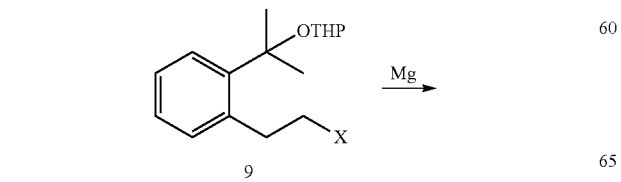

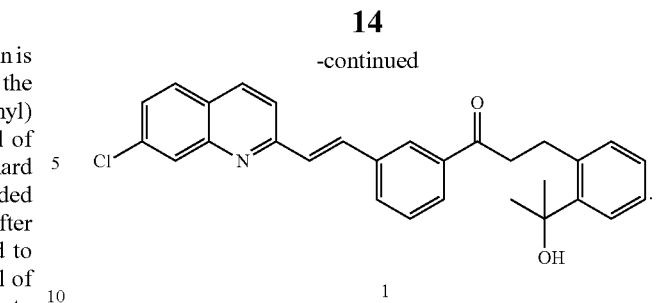

2. The method according to claim 1, wherein the compound of formula 4 is synthesized by the following steps:

(a) Condensing the compound of formula 2 with the compound of formula 3 under the existence of acetic anhydride and sodium acetate to generate the compound of formula 4, through the following reaction:

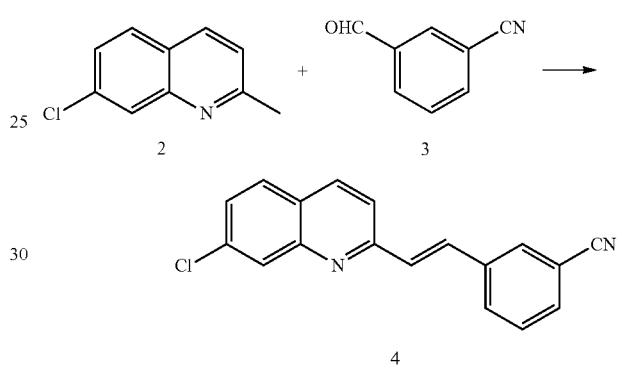

3. The method according to claim 1, wherein the compound of formula 9 is synthesized by the following steps:

(b) Reacting the compound of formula 5 in an inert solvent with methylmagnesium halide, to generate the compound of formula 6, through the following reaction:

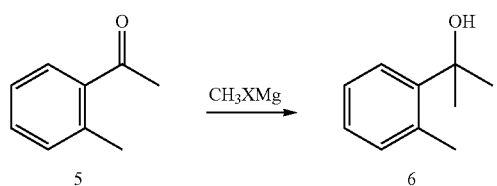

(c) Reacting the compound of formula 6 under the existence of a catalyst with dihydrodihydropyran to generate the compound of formula 7 with protection of hydroxyl, through the following reaction:

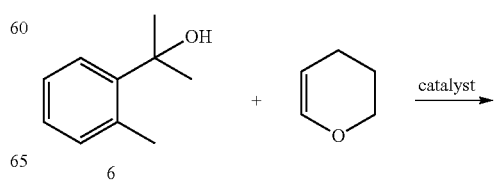

-continued

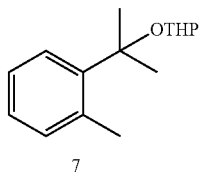

7

(d) Reacting the compound of formula 7 with formaldehyde or paraformaldehyde under the existence of a catalyst to generate the compound of formula 8, through the following reaction:

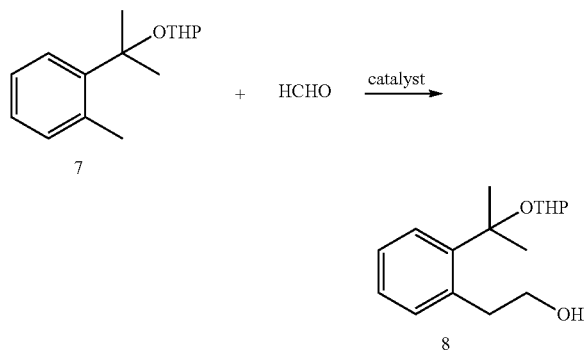

(e) Reacting the compound of formula 8 with a halogenating reagent to generate the compound of formula 9, through the following reaction:

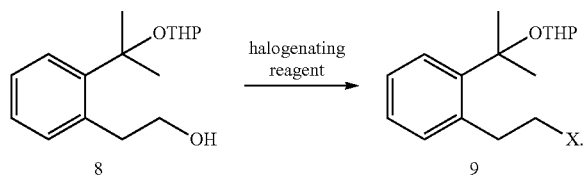

4. The method according to claim 3, wherein the reaction solvent in step (a) is one or more selected from the group consisting of dimethyl sulfoxide, acetic anhydride, dimethyl fomamide, dimethyl acetylamide and hexamethyl phosphoramide.

5. The method according to claim 4, wherein the reaction temperature in step (a) is 120° C.-140° C.

6. The method according to claim 5, wherein the methylmagnesium halide in step (b) is methylmagnesium chloride or methylmagnesium bromide.

7. The method according to claim 6, wherein the molar ratio among reactants in step (b) is methylmagnesium halide: the compound of formula 5=1:1.0-1.5.

8. The method according to claim 7, wherein the inert solvent in step (b) is one or more selected from the group consisting of benzene, tetrahydrofuran, 2-methyl-tetrahydrofuran, diethyl ether, isopropyl ether and ethylene glycol dimethyl ether.

9. The method according to claim 8, wherein the reaction temperature in step (b) is 20° C.-30° C.

10. The method according to claim 9, wherein the catalyst in step (c) is one or more selected from the group consisting of triphenylphosphine hydrobromide, tri-tertbutylphosphine hydrobromide, hydrochloric acid, hydrobromic acid, phosphorus oxychloride, p-toluenesulfonic acid and boron trifluoride-diethyl ether.

11. The method according to claim 10, wherein the catalyst in step (c) is triphenylphosphine hydrobromide.

12. The method according to claim 11, wherein the reaction solvent in step (c) is one or more selected from the group consisting of dichloromethane, chloroform, carbon tetrachloride, tetrahydrofuran, diethyl ether, dioxane, dimethyl fomamide and ethyl acetate.

13. The method according to claim 12, wherein the molar ratio among the reactants in step (c) is the compound of formula 6:dihydropyran:catalyst=1:2-6:0.1-1.

14. The method according to claim 13, wherein the reaction solvent in step (d) is one or more selected from the group consisting of dimethyl sulfoxide, dimethyl fomamide, dimethyl acetylamide and water.

15. The method according to claim 14, wherein the catalyst in step (d) is one selected from the group consisting of alkali metal hydroxide, alkali metal carbonate and organic quaternary ammonium hydroxide.

16. The method according to claim 15, wherein the molar ratio among reactants in step (d) is the compound of formula 7:catalyst:formaldehyde=1:0.001-0.1:1-4.

17. The method according to claim 16, wherein the reaction temperature in step (d) is 20° C.-100° C., while the reaction time is 1.5-24 hours.

18. The method according to claim 17, wherein the reaction solvent in step (e) is one or more selected from the group consisting of benzene, diethyl ether, dichloromethane, chloroform, carbon tetrachloride, dioxane and hexamethyl phosphoramide.

19. The method according to claim 18, wherein the halogenating reagent in step (e) is one or more selected from the group consisting of thionyl chloride, hydrochloric acid-zinc chloride, phosphorus pentachloride, phosphorus oxychloride, bromine hydride and phosphorus tribromide; while the reaction temperature is −5° C.-10° C.

20. The method according to claim 19, wherein the reaction in step (f) is carried out by adding dropwise, and during the adding dropwise the reaction temperature is controlled at 0° C.-5° C., while the molar ratio of reactants is the compound of formula 9:metal magnesium:the compound of formula 4=1: 1.2-2.5:0.8-1.

* * * * *